United States Patent [19]

Lau

[11] 4,333,999

[45] Jun. 8, 1982

[54] CYAN DYE-FORMING COUPLERS

[75] Inventor: Philip T. S. Lau, Rochester, N.Y.

[73] Assignee: Eastman Kodak Company, Rochester, N.Y.

[21] Appl. No.: 168,831

[22] Filed: Jul. 10, 1980

Related U.S. Application Data

[63] Continuation-in-part of Ser. No. 85,140, Oct. 15, 1979, abandoned.

[51] Int. Cl.³ .............................................. G03C 1/40
[52] U.S. Cl. .................................... 430/17; 430/384; 430/385; 430/552; 430/553
[58] Field of Search ................ 430/17, 384, 385, 552, 430/553

[56] References Cited

U.S. PATENT DOCUMENTS

| | | | |
|---|---|---|---|
| 3,446,622 | 5/1969 | Magagnoli et al. | 430/552 |
| 3,772,002 | 11/1973 | Ramello | 430/553 |
| 3,880,661 | 4/1975 | Lau et al. | 430/553 |
| 4,083,721 | 4/1978 | Inouye et al. | 430/552 |
| 4,254,212 | 3/1981 | Yagihara et al. | 430/553 |

*Primary Examiner*—J. Travis Brown
*Attorney, Agent, or Firm*—Joshua G. Levitt

[57] ABSTRACT

Novel phenolic cyan dye-forming couplers contain in the 2-position a p-cyanophenylureido group. These couplers are useful in photographic emulsions, elements and processes.

20 Claims, No Drawings

CYAN DYE-FORMING COUPLERS

This is a continuation-in-part of U.S. Pat. application Ser. No. 085,140 filed Oct. 15, 1979, now abandoned.

This invention relates to novel phenolic cyan dye-forming couplers, to photographic silver halide emulsions and elements containing these couplers, to processes of forming cyan dye images with elements containing these couplers and to processed elements containing cyan dyes derived from these couplers.

Color images are customarily obtained in the photographic art by reaction between the oxidation product of a silver halide color developing agent (i.e., oxidized aromatic primary amino developing agent) and a dye-forming compound known as a coupler. The reaction between coupler and oxidized color developing agent results in coupling of the oxidized color developing agent at a reactive site on the coupler, known as the coupling position, and yields a dye. The dyes produced by coupling are indoaniline, azomethine, indamine, or indophenol dyes, depending upon the chemical composition of the coupler and the developing agent. The subtractive process of color image formation is ordinarily employed in multicolored photographic elements and the dyes produced by coupling are usually cyan, magenta or yellow dyes which are formed in or adjacent silver halide emulsion layers sensitive to radiation absorbed by the image dye; i.e., silver halide emulsion layers sensitive to the red, green or blue regions of the spectrum.

The couplers which typically are employed to produce cyan dyes are phenols and naphthols. They yield azomethine dyes upon coupling with oxidized aromatic primary amino color developing agents.

Phenol couplers containing a ureido group in the 2-position are described in U.K. Pat. No. 1,011,940 and U.S. Pat. Nos. 3,446,622, 3,996,253, 3,758,308 and 3,880,661. These couplers generally have good light stability. However, many of them yield dyes having absorption maxima ($\lambda_{max}$) in the shorter wavelength portion of the red region of the spectrum or have relatively broad spectral absorption curves, or both. Thus, the dyes have undesirable hues for photographic purposes and frequently have significant absorption in the green region of the spectrum. In addition, a number of the dyes fade when contacted with ferrous ion and thus have poor stability in commonly employed processing compositions.

I have found a novel class of phenolic cyan dye-forming couplers which are characterized by a p-cyanophenylureido group in the 2-position of the phenol. Couplers of my invention yield dyes having absorption maxima ($\lambda_{max}$) in the longer wavelength portion of the red region of the visible spectrum (generally above 650 nm) and thus yield dyes of desirable hue for photographic images. Couplers of my invention yield dyes having relatively narrow spectral absorption curves and little absorption in the green region of the spectrum. Thus, they yield sharp cutting dyes of relatively pure hue. Couplers of my invention yield dyes which have excellent stability toward reduction by ferrous ion and hence can be used in processes employing bleach-fix baths containing ferrous ions without a significant reduction in cyan dye density. Couplers of my invention yield dyes which are stable to heat and light.

In one embodiment this invention relates to novel phenolic cyan dye-forming couplers having a p-cyanophenylureido group in the 2-position of the phenol.

In another embodiment this invention relates to photographic emulsions and elements containing these couplers.

In yet another embodiment this invention relates to processes of forming cyan dye images in photographic elements by developing the element in the presence of these couplers.

In still another embodiment this invention relates to processed photographic elements containing a cyan dye obtained by coupling of oxidized silver halide color developing agent and a coupler of this invention.

Advantageous couplers of this invention for incorporation in photographic emulsions and elements can be represented by the structural formula:

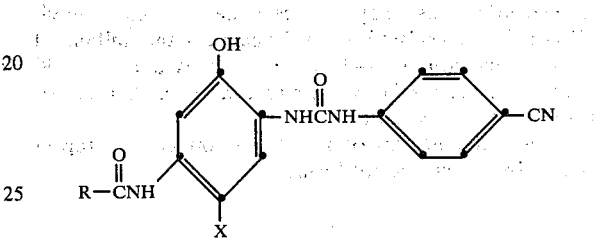

wherein:
X is hydrogen or a coupling-off group; and
R is a ballast group.

Coupling-off groups defined by X are well known to those skilled in the art. Such groups can determine the equivalency of the coupler (i.e., whether it is a two-equivalent coupler or a four-equivalent coupler), can modify the reactivity of the coupler, or can advantageously affect the layer in which the coupler is coated or other layers in the element by performing, after release from the coupler, such functions as development inhibition, bleach inhibition, bleach acceleration, color correction and the like. Representative classes of coupling-off groups include halogen, alkoxy, aryloxy, heteroyloxy, sulfonyloxy, acyloxy, acyl, heteroyl, thiocyano, alkylthio, arylthio, heteroylthio, sulfonamido, phosphonyloxy and arylazo. They are described, for example, in U.S. Pat. Nos. 2,455,169; 3,227,551; 3,432,521; 3,476,563; 3,617,291; 3,880,661; 4,052,212 and 4,134,766; and in U.K. patents and published applications Nos. 1,466,728; 1,531,927; 1,533,039; 2,006,755A and 2,017,704A; the disclosures of which are incorporated herein by reference.

Examples of specific coupling-off groups are:

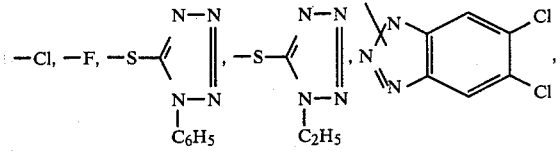

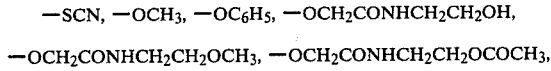

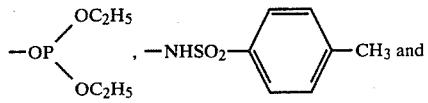

-continued

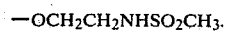

The ballast group defined by R is an organic radical of such size and configuration as to confer on the coupler molecule sufficient bulk to render the coupler substantially non-diffusible from the layer in which it is coated in a photographic element. Representative ballast groups include substituted or unsubstituted alkyl or aryl groups containing a total of 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents, and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido and sulfamoyl substituents contain 1–30 carbon atoms and 6 to 30 carbon atoms, respectively, and can be further substituted with such substituents.

Preferred couplers of this invention can be represented by the structural formula:

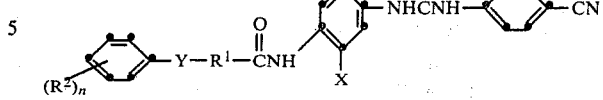

wherein:

X is hydrogen or a coupling-off group as defined above;

Y is oxygen or sulfur;

$R^1$ is a branched alkylene group of 2 to 20 carbon atoms, i.e., a secondary or tertiary alkylene;

$R^2$ is hydroxy, carboxy, alkyl, aryl, aralkyl, alkoxyl, aryloxy, alkylsulfamoyl, arylsulfamoyl, alkylsulfonamido, arylsulfonamido, alkylsulfonyl, arylsulfonyl, alkoxycarbonyl, or acyloxy wherein the alkyl moieties of these groups contain 1 to 20 carbon atoms and the aryl moieties contain 6 to 20 carbon atoms and wherein the alkyl, aryl and aralkyl moieties can be further substituted with hydroxy, carboxy, alkoxycarbonyl or acyloxy; and n is 1 to 3.

Especially preferred are those couplers where $R^2$ is straight or branched chain alkyl of 1 to 20 carbon atoms and n is 1 or 2.

Specific couplers of this invention are shown in Table I below with reference to Structure I above.

TABLE I

| Coupler Number | X | R |
|---|---|---|
| 1 | —H | —CHO—⟨⟩—$C_{15}H_{31}$—n, with $C_2H_5$ |
| 2 | —Cl | —CHO—⟨⟩—$C_{15}H_{31}$—n, with $C_2H_5$ |
| 3 | —H | —CHO—⟨⟩—$C_5H_{11}$—t, with $C_5H_{11}$—t and $C_8H_{17}$—n |
| 4 | —H | —CHO—⟨⟩—$C_5H_{11}$—t, with $C_5H_{11}$—t and $C_{12}H_{25}$—n |
| 5 | —H | —CHO—⟨⟩—$NHSO_2C_4H_9$—n, with $C_{12}H_{25}$—n |
| 6 | —H | —CHO—⟨⟩—$SO_2NHC_4H_9$—n, with $C_{12}H_{25}$—n |
| 7 | —H | —CHO—⟨⟩—$C_5H_{11}$—t, with $C_5H_{11}$—t and $C_4H_9$—n |
| 8 | —Cl | —CHO—⟨⟩—$C_5H_{11}$—t, with $C_5H_{11}$—t and $C_4H_9$—n |

TABLE I-continued

| Coupler Number | X | R |
|---|---|---|
| 9 | —H | —CHS—C₆H₄—OH, with —C₁₀H₂₁-n on CHS |
| 10 | —H | —CHS—C₆H₄—NHCOCH₃, with —C₁₀H₂₁-n on CHS |
| 11 | —Cl | —CHO—C₆H₃(C₅H₁₁-t)(C₅H₁₁-t), with —C₁₂H₂₅-n on CHO |
| 12 | —F | —CHO—C₆H₃(C₅H₁₁-t)(C₅H₁₁-t), with —C₄H₉-n on CHO |
| 13 | —H | —CHO—C₆H₄—COCH₃ (C=O), with —C₁₀H₂₁-n on CHO |
| 14 | —H | —CHO—C₆H₄—C(CH₃)₂—C₆H₄—OCCH₃ (O=), with —C₁₀H₂₁-n on CHO |
| 15 | —H | —CHO—C₆H₄—C(CH₃)₂—C₆H₄—OH, with —C₁₀H₁₁-n on CHO |
| 16 | —H | —CHO—C₆H₄—COOH, with —C₁₀H₂₁-n on CHO |
| 17 | —NHSO₂—C₆H₄—CH₃ | —CHO—C₆H₃(C₅H₁₁-t)(C₅H₁₁-t), with —C₄H₉-n on CHO |

Couplers of this invention can be prepared by reacting p-cyanophenylisocyanate with an appropriate aminophenol, such as 2-amino-5-nitrophenol or 2-amino-4-chloro-5-nitrophenol to form the 2-(p-cyanophenyl)ureido compound. The nitro group can then be reduced to an amine, and the ballast group attached thereto by conventional procedures. Additional two equivalent couplers can be prepared by known techniques, for example, by substitution of the 4-chloro group on the starting phenol reactant. Examples 1 and 2 show the preparation of representative couplers.

The cyan dye-forming couplers of this invention can be used in the ways and for the purposes that cyan dye-forming couplers are used in the photographic art.

Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent. Thus, as used herein, the term "associated therewith" signifies that the coupler is in the silver halide emulsion layer or in an adjacent location where, during processing, it will come into reactive association with silver halide development products.

The photographic elements can be single color elements or multicolor elements. In a multicolor element, the cyan dye-forming coupler of this invention would usually be associated with a red-sensitive emulsion, although it could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, incuding the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. patent application Ser. No. 8,819 filed Feb. 2, 1979.

A typical multicolor photographic element would comprise a support bearing a cyan dye image-forming unit comprised of at least one red-sensitive silver halide emulsion layer having associated therewith at least one cyan dye-forming coupler, at least one of the cyan dye-forming couplers being a coupler of this invention, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference will be made to Research Disclosure, December 1978, Item 17643, published by Industrial Opportunities Ltd., Homewell Havant, Hampshire, PO9 1EF, U.K., the disclosures of which are incorporated herein by reference. This publication will be identified hereafter by the term "Research Disclosure."

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. These couplers can be incorporated in the elements and emulsion as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-N,N-diethylaniline hydrochloride, 4-amino-3-methyl-N-ethyl-N-β-(methanesulfonamido)ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples further illustrate this invention.

EXAMPLE 1

Preparation of Coupler No. 7

A. Preparation of 2-(p-cyanophenyl)ureido-5-nitrophenol

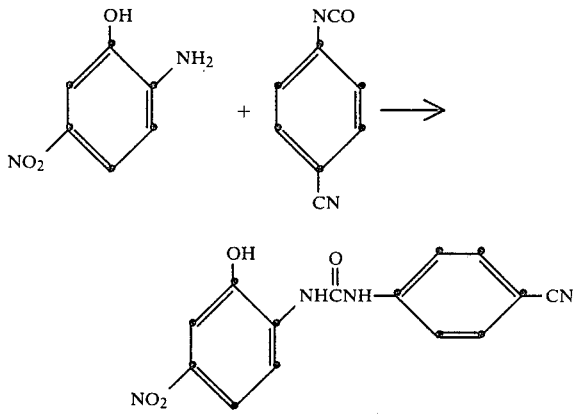

To a refluxing suspension of 23.1 g (0.15 mol) of 2-amino-5-nitrophenol in 300 ml. toluene was added with stirring a solution of 21.6 g (0.15 mol) p-cyanophenylisocyanate in 150 ml. toluene. The reaction mixture was refluxed for 1 hour. After cooling the yellow precipitate was collected, washed with hot toluene and then with dioxane to give 41 g (92%) of product; m.p. 262°–263° C.

B. Preparation of Coupler No. 7

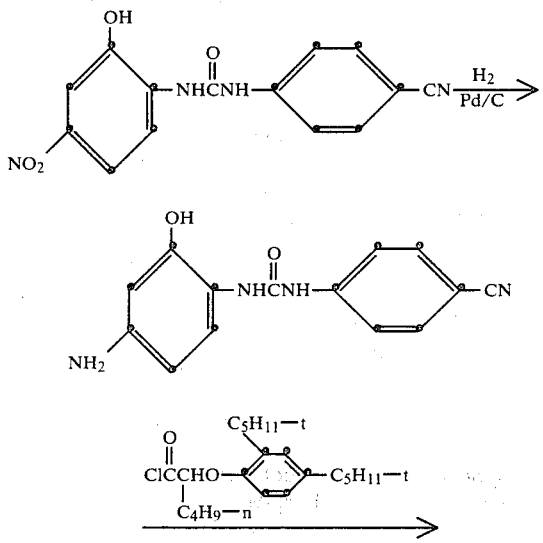

-continued

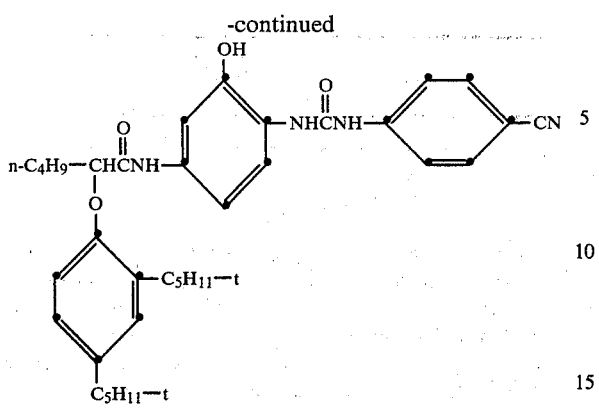

A suspension of 8.9 g (0.03 mol) of 2-(p-cyanophenyl)ureido-5-nitro phenol in 200 ml. tetrahydrofuran was catalytically reduced with a palladium on carbon catalyst under 40 psi of hydrogen. After the theoretical uptake of hydrogen, the mixture was blanketed with nitrogen gas as 7.8 g. (0.06 mol) of quinoline and 10.9 g. (0.03 mol) of 2-(2,4-di-tert-pentyl phenoxy)hexanoyl chloride was added with stirring. The reaction mixture was stirred overnight at 22° C. The mixture was filtered to remove the catalyst. The filtrate was poured into ice-water containing 5 ml. of concentrated hydrochloric acid, extracted with ether, dried over magnesium sulfate and concentrated under reduced pressure to give a gummy white solid and recrystallized from toluene to give 11.4 g (63%) of white crystalline solid; m.p. 177°–179° C.

EXAMPLE 2

Preparation of Coupler No. 11

A. Preparation of 2-(p-cyanophenyl)ureido-4-chloro-5-nitrophenol

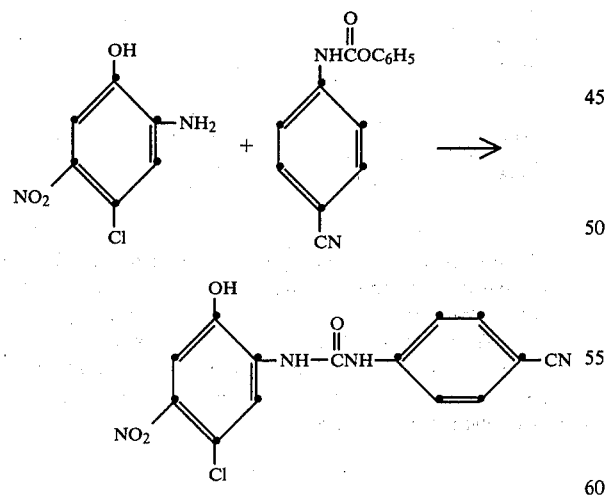

In a 1-liter flask was placed 37.6 g. (0.2 mol) of 2-amino-4-chloro-5-nitrophenol, 47.2 g. (0.2 mol) of phenyl p-cyanophenylcarbamate and 1.36 g. of imidazole in 400 ml. of xylene. The mixture was heated to reflux for 5 hours. The brown solid was collected, washed with xylene and then with hexane to give 64 g. (97%) brown solid; m.p. 227°–228° C.

B. Preparation of Coupler No. 11

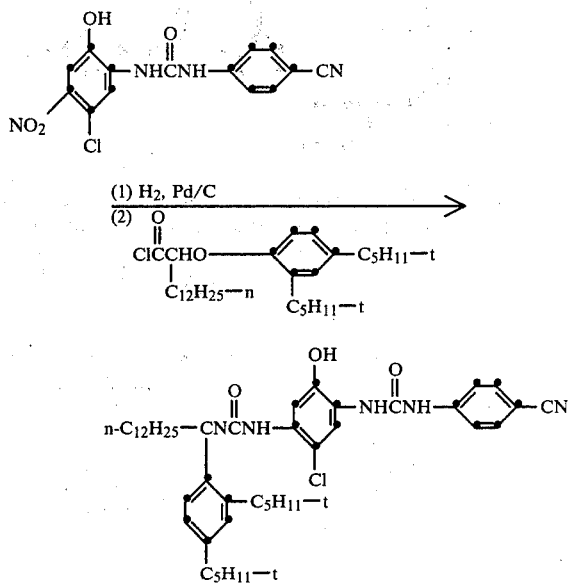

A suspension of 12 g. (0.036 mol) of 2-(p-cyanophenyl)ureido-4-chloro-5-nitrophenol and a teaspoonful of a palladium on carbon catalyst in 250 ml. of tetrahydrofuran was reduced under 40 psi of hydrogen. After the theoretical uptake of hydrogen, nitrogen was allowed to bubble in. With stirring, 10 g. of quinoline was added followed by 17.2 g. (0.036 mol) of 2-(2,4-di-tert-pentyl-phenoxy)tetradecanoyl chloride in 40 ml. of tetrahydrofuran. The reaction mixture was stirred at 22° C. for 3 hours and then filtered to remove the catalyst. The filtrate was poured into ice-water containing 10 ml. concentrated hydrochloric acid. The oil which separated was extracted with ethylacetate, dried over magnesium sulfate and concentrated under reduced pressure to give 28 g of residue. The crude product was taken up in methylene chloride and chromatographed through a silica gel column eluting with methylene chloride. The fractions containing the product were combined, concentrated under reduced pressure, and the residue recrystallized from acetonitrile to 11.4 g. of solid; m.p. 196°–198° C.

EXAMPLE 3

Photographic elements were prepared by coating a cellulose acetate film support with a light sensitive layer comprising a silver bromoiodide emulsion at 1.46 g Ag/m$^2$, gelatin at 4.86 g/m$^2$ and one of the following phenolic couplers at $1.68 \times 10^{-3}$ moles/m$^2$ dissolved in one half its weight of di-n-butylphthalate.

Coupler

Element A (control):

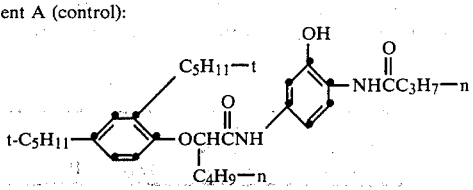

Element B (Coupler No. 7)

-continued

Coupler

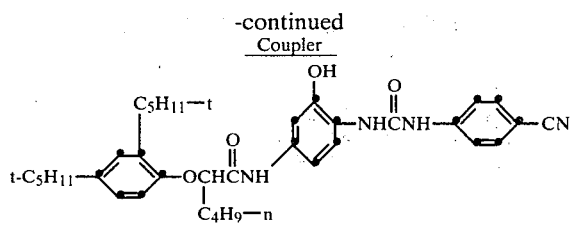

Samples of each element were sensitometrically exposed through a graduated-density test object and processed at 20° C. by color developing for 10 minutes with the following developer solution; then stopped, washed, bleached, washed, fixed and washed.

| Color Developer: | |
|---|---|
| Sodium hexametaphosphate | 0.5 g |
| Benzyl alcohol | 4.0 ml |
| $Na_2SO_3$ | 2.0 g |
| $Na_2CO_3 . H_2O$ | 50.0 g |
| NaOH (40% solution) | 0.4 ml |
| NaBr (50% solution) | 1.72 ml |
| 4-Amino-3-methyl-N-ethyl-N-β-(methanesulfonamido)ethylaniline sulfate hydrate | 5.0 g. |
| Water to 1 liter, pH 10.75. | |

Well-defined cyan dye images were produced. Sensitometric evaluation produced the following results:

| Element | $D_{max}$ | $\lambda_{max}$ |
|---|---|---|
| A | 2.67 | 657 nm |
| B | 2.73 | 689 nm |

EXAMPLE 4

Photographic elements were prepared by coating a cellulose acetate film support with a light-sensitive layer comprising a silver bromoiodide emulsion at a coverage dependent on coupler equivalency (see below), gelatin at 3.78 g/m², and a phenolic coupler (see below) at $1.62 \times 10^{-3}$ moles/m² dissolved in one half its weight of di-n-butylphthalate.

Samples of the elements were sensitometrically exposed through a graduated-density test object and processed at 20° C. as described in Example 3, except color development was for 2 minutes in the following developer solution:

| $K_2SO_3$ | 2.0 g |
|---|---|
| $K_2CO_3$ (anhydrous) | 30.0 g |
| KBr | 1.25 g |
| KI | 0.6 mg |
| 4-Amino-3-methyl-N-ethyl-N-β-hydroxyethylaniline sulfate | 3.55 g |
| Water to 1.0 liter, pH 10.0. | |

Well-defined cyan dye images were produced which were sensitometrically evaluated. The results are recorded below.

| Element | Coupler No. | Ag Coverage (g/m²) | $D_{max}$ | $D_{min}$ | $\lambda_{max}$ |
|---|---|---|---|---|---|
| C | 7 | 0.91 | 2.97 | 0.09 | 690 |
| D | 12 | 0.46 | 2.72 | 0.06 | 685 |

-continued

| Element | Coupler No. | Ag Coverage (g/m²) | $D_{max}$ | $D_{min}$ | $\lambda_{max}$ |
|---|---|---|---|---|---|
| E | 13 | 0.91 | 3.10 | 0.09 | 695 |

EXAMPLE 5

A series of photographic elements was prepared, exposed and processed as described in Example 3, above, using the couplers identified below. Well-defined cyan dye images were produced. From the developed images spectrophotometric curves having a maximum density of 1.0 were generated and the wavelength of maximum dye density ($\lambda_{max}$) and the half-band width (HBW) were determined. Half-band width is the width in nanometers of the spectrophotometric curve at one half the difference between maximum density and dye fog. It is a measure of the purity of the hue of the dye; the narrower half-band width, the purer the hue.

The following results were obtained.

| Element | Coupler | λ max (nm) | HBW (nm) |
|---|---|---|---|
| F | 1 | 664 | 127 |
| G | 7 | 688 | 142 |
| H | A* | 668 | 148 |
| I | B* | 659 | 159 |
| J | C* | 644 | 137 |

*Coupler A is coupler 33 from U.S. Pat. No. 3,880,661 and has the structure:

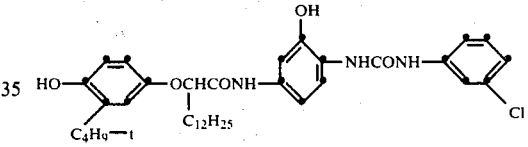

Coupler B is compound IV from U.S. Pat. No. 3,758,308 and has the structure:

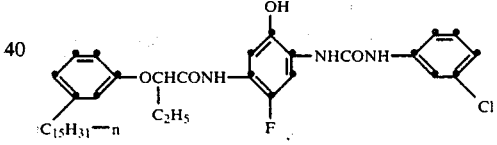

Coupler C is a non-ureido coupler having the structure:

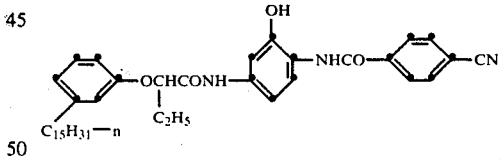

This data indicates that dyes derived from couplers of the present invention absorb at longer wavelengths and/or have narrower half-band width than dyes derived from structurally close couplers which do not contain a p-cyanophenylureido group. Thus, the dyes from the present couplers have desirable and relatively pure absorption in the red region of the spectrum.

EXAMPLE 6

A series of photographic elements was prepared, exposed and processed as described in Example 4, above, using the couplers identified below. Well-defined cyan dye images were obtained. From the developed images spectrophotometric curves having a maximum density of 1.0 were generated, from which λmax and HBW were determined.

The results are reported below.

| Element | Coupler | λ max (nm) | HBW |
|---|---|---|---|
| N | 7 | 690 | 141 |
| O | D* | 694 | 177 |

*Coupler D is coupler VII from U.S. Pat. No. 3,996,253 and has the structure:

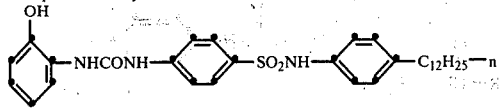

This data indicates that the inventive dye has a narrower half-band width than the prior art dye and thus is a sharper cutting dye of purer hue.

EXAMPLE 7

Dye stability toward reduction by ferrous ions was determined by treating a processed samples of each of Elements N and O from Example 6 in a ferrous ion containing solution in the following manner. A suspension was prepared by adding 32.12 g (0.11 mole) ethylenediamine tetraacetic acid to 750 ml concentrated ammonium hydroxide. To this suspension was added 27.8 g (0.10 mole) of ferrous sulfate heptahydrate with stirring and then concentrated ammonium hydroxide was slowly added until a solution was obtained. The pH was then adjusted to 5.0 with nitric acid.

The samples were immersed in the above solution for 5 minutes at room temperature, washed in water for 5 minutes and dried. When compared to untreated samples, the following results were obtained.

| Element | $D_{max}$ Untreated | $D_{max}$ Treated | % Dye Loss |
|---|---|---|---|
| N | 2.16 | 2.08 | 3.7% |
| O | 2.30 | 0.19 | 91.7% |

EXAMPLE 8

Photographic elements containing additional couplers of this invention were prepared, exposed and processed as in Example 4 and then spectrophotometric curves were generated and $\lambda_{max}$ and HBW were determined as in Example 5. The results are show below.

| Coupler | λ max | HBW |
|---|---|---|
| 5 | 675 | 136 |
| 6 | 655 | 153 |
| 8 | 691 | 135 |
| 9 | 674 | 151 |
| 11 | 695 | 137 |
| 12 | 691 | 133 |
| 13 | 685 | 141 |
| 14 | 684 | 133 |
| 15 | 681 | 136 |
| 16 | 669 | 152 |

This data indicates that couplers of this invention, as a class, yield dyes having absorption maxima in the longer wavelength portion of the red region of the visible spectrum and generally have relatively narrow half-band widths. Thus, the dyes have little or no absorption in the green region of the spectrum and have relatively pure hues that are desirable for photographic images.

This invention has been described in detail with particular reference to preferred embodiments thereof but it will be understood that variations and modifications can be effected within the spirit and scope of the invention.

What is claimed is:

1. A photographic element comprising a support and a photographic silver halide emulsion having associated therewith a cyan dye-forming coupler having the structure:

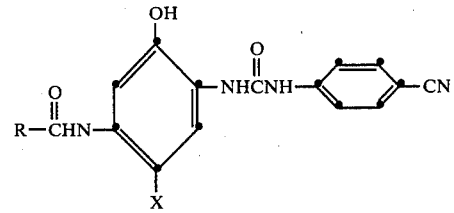

wherein:
X is hydrogen or a coupling-off group; and
R is a ballast group.

2. A photographic element of claim 1 wherein the cyan dye-forming coupler has the structure:

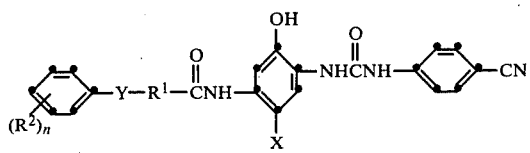

wherein:
X is hydrogen or a coupling-off group;
Y is oxygen or sulfur;
$R^1$ is a branched alkylene group of 2 to 20 carbon atoms;
$R^2$ is hydroxy, carboxy, alkyl, aryl, aralkyl, alkoxyl, aryloxy, alkylsulfamoyl, arylsulfamoyl, alkylsulfonamido, arylsulfonamido, alkylsulfonyl, arylsulfonyl, alkoxycarbonyl, or acyloxy wherein the alkyl moieties of these groups contain 1 to 20 carbon atoms and the aryl moieties contain 6 to 20 carbon atoms and wherein the alkyl, aryl and aralkyl moieties can be further substituted with hydroxy, carboxy, alkoxycarbonyl or acyloxy; and
n is 1 to 3.

3. A photographic element of claim 2 wherein:
X is hydrogen or a coupling-off group;
Y is oxygen;
$R^2$ is alkyl of 1 to 20 carbon atoms; and
n is 1 or 2.

4. A photographic element of claim 1 wherein the cyan dye-forming coupler has the structure:

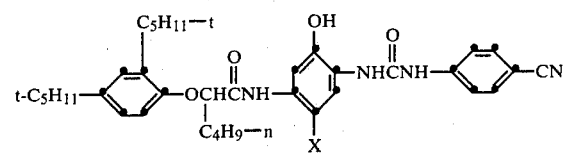

wherein X is hydrogen or a coupling-off group.

5. A photographic element of claim 4 wherein the cyan dye-forming coupler has the structure:

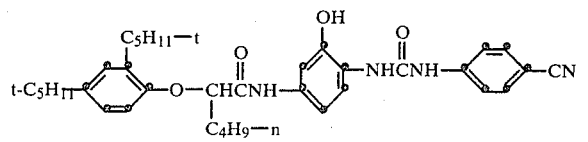

6. A photographic element of claim 1 wherein the cyan dye-forming coupler has the structure:

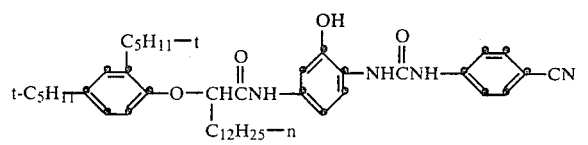

7. A photographic silver halide emulsion containing a cyan dye-forming coupler having the structure:

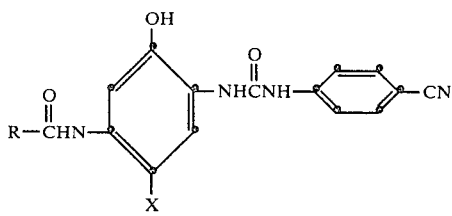

wherein:
X is hydrogen or a coupling-off group; and
R is a ballast group.

8. A photographic emulsion of claim 7 wherein the cyan dye-forming coupler has the structure:

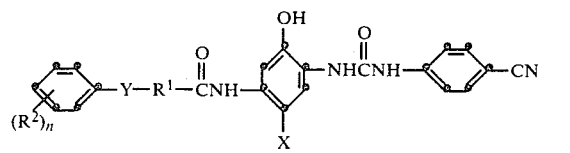

wherein:
X is hydrogen or a coupling-off group;
Y is oxygen or sulfur;
$R^1$ is a branched chain alkylene group of 2 to 20 carbon atoms;
$R^2$ is hydroxy, carboxy, alkyl, aryl, aralkyl, alkoxyl, aryloxy, alkylsulfamoyl, arylsulfamoyl, alkylsulfonamido, arylsulfonamido, alkylsulfonyl, arylsulfonyl, alkoxycarbonyl, or acyloxy wherein the alkyl moieties of these groups contain 1 to 20 carbon atoms and the aryl moieties contain 6 to 20 carbon atoms and wherein the alkyl, aryl and aralkyl moieties can be further substituted with hydroxy, carboxy, alkoxycarbonyl or acyloxy; and
n is 1 to 3.

9. A photographic emulsion of claim 8 wherein:
X is hydrogen or a coupling-off group;
Y is oxygen;
$R^2$ is alkyl of 1 to 20 carbon atoms; and
n is 1 or 2.

10. A process of forming a cyan dye image in a photographic element comprising a support and a silver halide emulsion, comprising the step of developing the element with a silver halide color developing agent in the presence of a cyan dye-forming coupler having the structure:

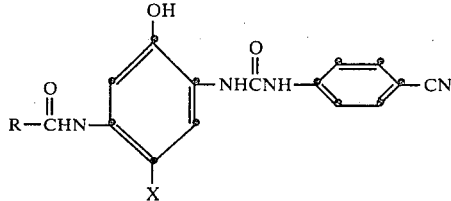

wherein:
X is hydrogen or a coupling-off group; and
R is a ballast group.

11. A process of claim 10 wherein the color developing agent is a p-phenylenediamine.

12. A process of claim 11 wherein the cyan dye-forming coupler has the structure:

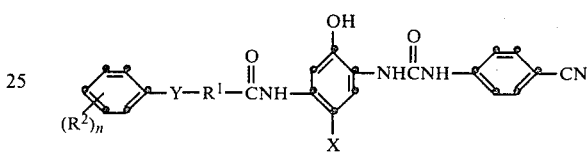

wherein:
X is hydrogen or a coupling-off group;
Y is oxygen or sulfur;
$R^1$ is a branched alkylene group of 2 to 20 carbon atoms;
$R^2$ is hydroxy, carboxy, alkyl, aryl, aralkyl, alkoxyl, aryloxy, alkylsulfamoyl, arylsulfamoyl, alkylsulfonamido, arylsulfonamido, alkylsulfonyl, arylsulfonyl, alkoxycarbonyl, or acyloxy wherein the alkyl moieties of these groups contain 1 to 20 carbon atoms and the aryl moieties contain 6 to 20 carbon atoms and wherein the alkyl, aryl and aralkyl moieties can be further substituted with hydroxy, carboxy, alkoxycarbonyl or acyloxy; and
n is 1 to 3.

13. A process of claim 12 wherein:
X is hydrogen or a coupling-off group;
Y is oxygen;
$R^2$ is alkyl of 1 to 20 carbon atoms; and
n is 1 or 2.

14. A process of claim 13 wherein the cyan dye-forming coupler has the structure:

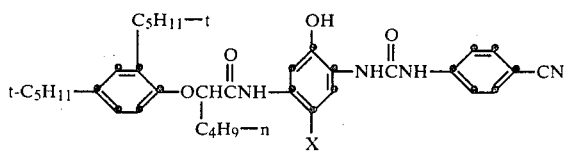

wherein:
X is hydrogen or a coupling-off group.

15. A processed photographic element containing a cyan dye image comprised of a cyan dye obtained by coupling of oxidized silver halide color developing agent and a cyan dye-forming coupler having the structure:

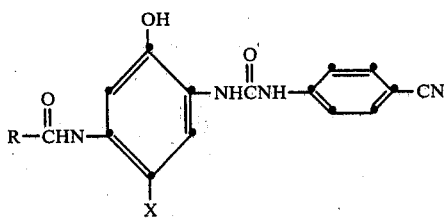

wherein:
X is hydrogen or a coupling-off group; and
R is a ballast group.

16. A processed photographic element of claim 15 wherein the cyan dye-forming coupler has the structure:

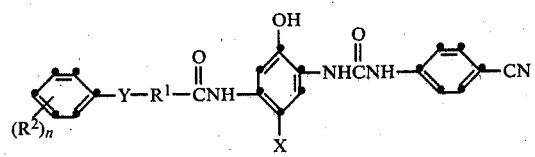

wherein:
X is hydrogen or a coupling-off group;
Y is oxygen or sulfur;
$R^1$ is a branched alkylene group of 2 to 20 carbon atoms;
$R^2$ is hydroxy, carboxy, alkyl, aryl, aralkyl, alkoxyl, aryloxy, alkylsulfamoyl, arylsulfamoyl, alkylsulfonamido, arylsulfonamido, alkylsulfonyl, arylsulfonyl, alkoxycarbonyl, or acyloxy wherein the alkyl moieties of these groups contain 1 to 20 carbon atoms and the aryl moieties contain 6 to 20 carbon atoms and wherein the alkyl, aryl and aralkyl moieties can be further substituted with hydroxy, carboxy, alkoxycarbonyl or acyloxy; and
n is 1 to 3.

17. A processed photographic element of claim 16 wherein:
X is hydrogen or a coupling-off group;
Y is oxygen;
$R^2$ is alkyl of 1 to 20 carbon atoms; and
n is 1 or 2.

18. A processed photographic element of claim 17 wherein the cyan dye-forming coupler has the structure:

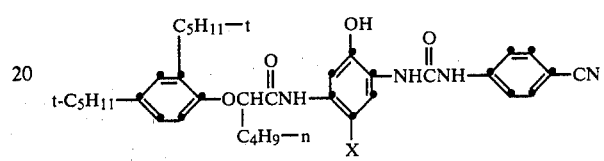

wherein X is hydrogen or a coupling-off group.

19. A processed photographic element of any one of claims 15, 16, 17 or 18 wherein the color developing agent is a p-phenylenediamine.

20. A processed photographic element of claim 18 wherein the color developing agent is
4-amino-3-methyl-N-ethyl-N-β-hydroxyethylaniline sulfate.

* * * * *